(12) United States Patent
Tarnopolsky (10) Patent No.: US 12,419,852 B2
(45) Date of Patent: Sep. 23, 2025

(54) METHOD FOR TREATING LYSOSOMAL STORAGE DISEASE

(71) Applicant: Exerkine Corporation, Hamilton (CA)

(72) Inventor: Mark Tarnopolsky, Hamilton (CA)

(73) Assignee: Exerkine Corporation, Ontario (CA)

( * ) Notice: Subject to any disclaimer, the term of this patent is extended or adjusted under 35 U.S.C. 154(b) by 994 days.

(21) Appl. No.: 17/271,671

(22) PCT Filed: Aug. 27, 2019

(86) PCT No.: PCT/CA2019/051178
§ 371 (c)(1),
(2) Date: Feb. 26, 2021

(87) PCT Pub. No.: WO2020/041871
PCT Pub. Date: Mar. 5, 2020

(65) Prior Publication Data
US 2021/0322358 A1    Oct. 21, 2021

Related U.S. Application Data

(60) Provisional application No. 62/723,056, filed on Aug. 27, 2018.

(51) Int. Cl.
| | |
|---|---|
| *A61K 31/225* | (2006.01) |
| *A61K 31/047* | (2006.01) |
| *A61K 31/198* | (2006.01) |
| *A61K 31/352* | (2006.01) |
| *A61K 36/74* | (2006.01) |
| *A61K 36/82* | (2006.01) |
| *A61K 45/06* | (2006.01) |
| *A61P 21/00* | (2006.01) |

(52) U.S. Cl.
CPC .......... *A61K 31/225* (2013.01); *A61K 31/047* (2013.01); *A61K 31/198* (2013.01); *A61K 31/352* (2013.01); *A61K 36/74* (2013.01); *A61K 36/82* (2013.01); *A61K 45/06* (2013.01); *A61P 21/00* (2018.01)

(58) Field of Classification Search
CPC .. A61K 31/225; A61K 31/047; A61K 31/198; A61K 31/352; A61K 36/74; A61K 36/82; A61K 45/06; A61P 21/00
See application file for complete search history.

(56) References Cited

U.S. PATENT DOCUMENTS

| | | | |
|---|---|---|---|
| 9,138,420 B2 | 9/2015 | D Agostino et al. | |
| 2006/0004099 A1* | 1/2006 | Roe | A23L 33/16 514/558 |
| 2020/0397792 A1* | 12/2020 | Millet | A61K 31/353 |
| 2021/0205241 A1* | 7/2021 | Millet | A61K 45/06 |

FOREIGN PATENT DOCUMENTS

| | | |
|---|---|---|
| CA | 2801206 A1 | 12/2011 |
| WO | 2015073816 A1 | 5/2015 |
| WO | 2017/165445 A1 | 9/2017 |
| WO | 2018/081118 A1 | 5/2018 |

OTHER PUBLICATIONS

HMDB. (2017). Human Metabolome database. Metabocard for 1,3-Butanediol (HMDB0031320) (Year: 2017).*
Pravst, Igor, Katja Žmitek, and Janko Žmitek. "Coenzyme Q10 contents in foods and fortification strategies." Critical reviews in food science and nutrition 50.4 (2010): 269-280. (Year: 2010).*
Frontiers in pharmacology 2 (2011): 15229.) (Year: 2011).*
Free Radical Biology and Medicine. 72 (2014) 76-90. (Year: 2014).*
Journal of animal physiology and animal nutrition 99.3 (2015): 405-417. (Year: 2015).*
Nutrition 29.3 (2013): 479-484. (Year: 2013).*
Neurochemical research 41 (2016): 600-609. (Year: 2016).*
Nutrients 8.8 (2016): 506. (Year: 2016).*
Folkers et al. Proceedings of the National Academy of Sciences 82.13 (1985): 4513-4516. (Year: 1985).*
PloS one 8.4 (2013): e60722. (Year: 2013).*
Denny et al.—"Restricted ketogenic diet enhances the therapeutic action of N-butyldeoxynojirimycin towards brain GM2 accumulation in adult Sandhoff disease mice", J Neurochem. Jun. 2010;113(6):1525-35.
Denny et al.—"Influence of caloric restriction on motor behavior, longevity, and brain lipid composition in Sandhoff disease mice", J Neurosci Res. May 1, 2006;83(6):1028-38.
Scott et al.—"The effect of 1,3-butanediol and carbohydrate supplementation on running performance", Journal of Science and Medicine in Sport. vol. 22, Issue 6, Jun. 2019, pp. 702-706.
Extended European Search Report—Application No. 19855082.4 May 2, 2022.
Valayannopoulos et al.—Successful Treatment of Severe Cardiomyopathy in Glycogen Storage Disease Type III with D, L-3-Hydroxybutyrate, Ketogenic and High-Protein Diet, Pediatric Research, vol. 70, No. 6, Dec. 1, 2011, pp. 638-641.
Angelini Corrado et al.—Therapeutic advances in the management of Pompe disease and other metabolic myopathies, Therapeutic advances in Neurological Disorders May 2010, vol. 6, No. 5, Sep. 1, 2013, pp. 311-321.
Tarnopolsky et al.—Nutrition and exercise in Pompe disease, Annals of Translational Medicine, vol. 7, No. 13, Jul. 1, 2019, p. 282.
Kieran Clarke et al.—Kinetics, safety and tolerability of ()-3-hydroxybutyl ()3-hydroxybutyrate in healthy adult subjects, Regulatory Toxicology and Pharmacology, vol. 63, No. 3 May 3, 2012.
International Search Report—PCT/CA2019/051178 dated Nov. 12, 2019.

(Continued)

*Primary Examiner* — Kamal A Saeed
*Assistant Examiner* — Quincy McKoy
(74) *Attorney, Agent, or Firm* — Gowling WLG (Canada) LLP (57) ABSTRACT

This application is directed to the use of a ketogenic agent, such as 1,3-butanediol, R-β-hydroxybutyl-R-β-hydroxybutyrate, or triheptanoin, in the treatment of an individual having a lysosomal storage disease, including Pompe disease. Compositions comprising ketogenic agents and metabolic enhancing agents for treating a lysosomal storage disease are also provided.

15 Claims, 3 Drawing Sheets

(56) References Cited

OTHER PUBLICATIONS

Written Opinion—PCT/CA2019/051178 dated Nov. 12, 2019.
Bhattacharya et al.—"Dietary Management of the Ketogenic Glycogen Storage Diseases", Journal of Inborn Errors of Metabolism and Screening, 4, pp. 1-6 Sep. 26, 2016.
Villamizar-Schiller et al.—"Neurological and Cardiac Responses after Treatment with Miglustat and a Ketogenic Diet in Patient with Sandhoff Disease", European Journal of Medical Genetics, 58(3), pp. 180-183 Mar. 2015.

* cited by examiner

METHOD FOR TREATING LYSOSOMAL STORAGE DISEASE

FIELD OF THE INVENTION

The present invention generally relates to lysosomal storage disease, and more particularly relates to the use of a ketogenic agent for the treatment of lysosomal storage disease in a mammal.

BACKGROUND OF THE INVENTION

Lysosomes are cellular organelles that function as a cellular waste disposal mechanism to remove unused, damaged, or excessive macro-molecules. There are at least fifty lysosomal enzymes that are known to function in the acidic environment of the lysosome (pH approximately 4.0-5.0) to break down cellular macro-molecules including; lipids, carbohydrates, glycolipids, proteins, nucleic acids and organelles such as mitochondria (mitophagy). In addition to the removal of accumulated cellular debris, the lysosomal pathway is also involved in a variety of cellular processes including cell secretion, signalling cascades, energy metabolism, plasma membrane repair, and mitochondrial homeostasis. The enzymes within lysosomes are encoded by nuclear DNA, transcribed on ribosomes in the rough endoplasmic reticulum, and subsequently targeted to the Golgi apparatus where they are packaged and released in small vesicles that ultimately fuse with endosomes to form lysosomes.

Lysosomal storage diseases are disorders resulting from gene mutations that lead to a defective, non-functional lysosomal protein (enzyme). There are over two dozen known genetic diseases that affect the lysosome. In general, specific genetic mutations negatively affect the ability of the hydrolytic enzymes within the lysosome to perform their function, thus leading to the accumulation of the precursor products for that enzyme. This aggregation of the intra-lysosomal precursor protein perpetuates downstream cellular consequences including the displacement of normal cellular contents and/or disruption of the lysosomes that can cause the release of hydrolytic enzymes into the cytosol which may damage other macromolecules crucial for cellular metabolism, redox homeostasis, and survival.

One example of a lysosomal storage disease is Pompe disease that results from a genetic mutation in the protein acid alpha-glucosidase (GAA). Genetic mutations that impact the GAA protein result in a progressive build-up of glycogen in skeletal and cardiac muscle that culminates in: (A) an infantile form with cardiomyopathy, respiratory failure and weakness, or (B) a late onset form which leads to muscle weakness and eventually respiratory failure.

Until recently, therapy for lysosomal storage disease was designed to treat the clinical manifestations of the disease (i.e., canes, walkers and wheelchairs for weakness and non-invasive and invasive ventilation for respiratory insufficiency), rather than addressing the underlying cause of the lysosomal storage disease. More recently, a therapeutic strategy has been employed to specifically address and alleviate the enzymatic deficiency that leads to lysosomal storage disease by directly replacing the defective enzyme through intravenous infusion, called enzyme replacement therapy (ERT). ERT operates on the premise that the pathology specific defective lysosomal enzyme is replaced through direct infusion of the specific enzyme into the circulation. This infused enzyme, produced via recombinant protein technology, is then taken up by mannose-6-phosphate receptors on the cell surface. Once inside the cell, the protein can be internalized through mannose-6-phosphate receptors on lysosomes, and thereby replace the defective enzyme.

There are a variety of issues that can arise with enzyme replacement therapy that limit its effectiveness. Firstly, the pH of the lysosomes is quite low whereas blood is usually at a pH of 7.4. Consequently, the infused enzyme is exposed to a non-native pH environment that causes it to denature, leading to a rapid elimination of the infused protein from the circulation. Therefore, the bioavailability of the infused enzyme is quite low as the total exposure to the affected tissues is limited. It has been estimated that only a small fraction (1-3%) of the infused recombinant GAA protein in Pompe disease is actually retained within skeletal muscle 2 weeks after the infusion. Secondly, there is a vast difference between different tissues with respect to their ability to respond to ERT. Skeletal muscle (especially type II fibers) is much more resistant to ERT therapy in comparison to cardiac muscle, when ERT is used in Pompe disease treatment for example.

In addition to the accumulation of non-degraded substrate within the lysosomes, it is also known that some of the pathophysiological consequences of LSDs comes from the impairment of the lysosomal dependent process called autophagy. An impairment in autophagy can result in the accumulation of dysfunctional proteins within the cell that can impair cellular and organismal function, including the uptake and transport of ERT.

Given the limitations of ERT and the evidence for impaired autophagy in LSDs, it would be desirable to provide an improved method for the treatment of lysosomal storage disease.

SUMMARY OF THE INVENTION

It has now been determined that the administration of a ketogenic agent is therapeutically useful for improving muscle function, autophagic activity and mitochondrial capacity in an individual having a lysosomal storage disease.

Thus, in a first embodiment of the present invention a method of treating an individual with a lysosomal storage disease is provided comprising administering to the individual a ketogenic agent.

In another embodiment of the present disclosure a method of improving at least one of muscle function, autophagic activity and mitochondrial capacity in an individual having a lysosomal storage disease is provided comprising administering to the individual a ketogenic agent.

In another embodiment, a method of treating a lysosomal storage disease in an individual is provided, wherein the method comprises administering to the individual a ketogenic agent in conjunction with enzyme replacement therapy.

In another embodiment, a method for the treatment of a lysosomal storage disease in an individual is provided comprising administering an enhanced ketogenic composition to the individual, wherein the enhanced ketogenic composition comprises a ketogenic agent and a metabolic enhancing agent.

In another embodiment, a composition for treating a lysosomal storage disease is provided, comprising a ketogenic agent and a metabolic enhancing agent.

In another embodiment, a composition for treating a lysosomal storage disease is provided, comprising a ketogenic agent, and a metabolic enhancing agent comprising a mitochondria enhancing agent, a weight loss agent, a muscle mass preservation agent and a nitric oxide precursor.

These and other aspects of the present invention will become apparent in the detailed description that follows, by reference to the following figures.

DETAILED DESCRIPTION OF THE INVENTION

A method of treating an individual with a lysosomal storage disease is provided comprising administering to the individual a ketogenic agent.

The term "ketogenic agent" as used herein, refers to any compound which increases the concentration of ketone bodies in an individual. The ketogenic agent for use in the present composition may be selected from any physiologically acceptable source of ketone bodies including a ketone body, a ketone salt, a ketone ester, a ketone oligomer, a ketone body precursor or derivative thereof and any combination thereof. Non-limiting examples of ketone bodies include beta-hydroxybutyrate and acetoacetate in the free acid form. Beta-hydroxybutyrate may be administered in the racemic form, or preferably, in the R-beta-hydroxybutyrate form. Non-limiting examples of ketone salts include arginine, calcium, ornithine, potassium, citrulline, magnesium, sodium, magnesium, agmatine, lithium, histidine, creatine and lysine salts of beta-hydroxybutyrate. Non-limiting examples of ketone esters include 1,3-butanediol (such as racemic or preferably, R-1,3-butanediol), R-beta hydroxybutyl R-beta hydroxybutyrate, monoesters or diesters of beta-hydroxybutyrate with glycerol, 1,3-butanediol acetoacetate monoesters (such as R,S-1,3-butanediol-monoacetoacetate ester), 1,3-butanediol acetoacetate diesters (such as R-1,3-butanediol diacetoacetate ester), monoacetoacetin and triacetoacetin. Non-limiting examples of ketone oligomers include dimers and trimers of beta-hydroxybutyrate or 1,3-butanediol. Non-limiting examples of ketone precursors include odd-chain fatty acids (such as triheptanoin) and even-chain fatty acids.

The term "individual" is used herein to refer to a mammal, including human and non-human mammals.

The terms "treat", "treating" or "treatment" are used herein to refer to methods that favourably alter a lysosomal storage disease, including those that moderate, reverse, reduce the severity of, or protect against, the progression of a lysosomal storage disease. Thus, for use to treat such a disease, a therapeutically effective amount of a ketogenic agent, useful to treat the disease, is administered to an individual. The term "therapeutically effective amount" is an amount of ketogenic agent required to treat the clinical impact of the disease, while not exceeding an amount that may cause significant adverse effects. Dosages of ketogenic agents that are therapeutically effective will vary on many factors including the nature of the condition to be treated as well as the particular individual being treated. Appropriate ketogenic agent dosages for use include dosages sufficient to result in blood ketone body concentrations of between about 0.1 mM to about 25 mM, such as about 0.3 mM to about 8 mM, or about 0.4 mM to about 2 mM. For example, in one embodiment, the dosage may be a dosage in an amount in the range of about 0.001 g/kg of body weight to about 5 g/kg of body weight per day, such as about 0.01 g/kg body weight to about 0.2 g/kg body weight per day. In another embodiment, the dosage of ketogenic agent administered may be an amount which equals about 0.1-10% of the diet, such as 0.5-3% of the diet. The term "about" is used herein to mean an amount that may differ somewhat from the given value, by an amount that would not be expected to significantly affect activity or outcome as appreciated by one of skill in the art, for example, a variance of from 1-10% from the given value.

In one embodiment, an enhanced ketogenic composition comprising a ketogenic agent and a metabolic enhancing agent is provided and is useful for treating lysosomal storage disease.

The metabolic enhancing agent is comprised of at least one of a mitochondria enhancing agent, a weight loss agent, a muscle mass preservation agent and a nitric oxide precursor. In one embodiment, the ketogenic agent comprises about 0.1-90% of the dry weight of the enhanced ketogenic composition, such as about 1-80%, or about 5-50% of the dry weight of the composition.

The metabolic enhancing agent may comprise at least one mitochondria enhancing agent. The mitochondria enhancing agent may be selected from any suitable agent that promotes mitochondrial capacity in a mammal, for example, by increasing the abundance of mitochondria, increasing the ATP generating capacity of mitochondria, protecting mitochondria from excessive oxidative stress, promoting the maintenance of mitochondrial components, ion gradients and ultrastructure, such as through increased mitochondrial autophagy (mitophagy) events or increased mitochondrial fission and fusion events or by preventing the accumulation of less functional mitochondrial occurring in response to a pathological stimulus.

In one embodiment, the mitochondria enhancing agent is selected from at least one of the following: beetroot extract, nitrates, idebenone, nicotinamide riboside, elamepratide, vitamin C, vitamin D, vitamin E, thiamine, riboflavin, magnesium, calcium, phosphate, membrane phospholipids, creatine, pyruvate, coenzyme Q10, NADH, nicotinic acid, l-carnitine, dichloroacetate, curcumin, schisandrin, quercetin, resveratrol and mixtures thereof.

In one embodiment the mitochondria enhancing agent comprises a mixture of beetroot extract, coenzyme Q10, alpha lipoic acid, creatine and vitamin E.

In another embodiment, the mitochondria enhancing agent comprises a mixture of beetroot extract, coenzyme Q10, alpha lipoic acid and vitamin E.

The beetroot extract for use in the present composition may be selected from any suitable beetroot source including red beets such as Detroit Dark Red, Red Ace, Early Wonder Tall Top, Bull's Blood, Forono, Ruby Queen, Chioggia, Cylindra or Gladiator, yellow or gold beets such as Yellow Detroit, Golden, Touchstone Gold or Boldor or white beets such as Avalanche, Baby White, Blankoma or Sugar. Preferably, the beetroot extract is substantially derived from the taproot portion of the beetroot. In one embodiment, the beetroot extract for use in the present composition comprises at least about 1.5% nitrates by dry weight. In another embodiment, the beetroot extract comprises about 0.01-25% of the dry weight of the enhanced ketogenic composition, such as about 0.1-10%, or about 0.5-5% of the dry weight of the composition. In another embodiment, the beetroot extract comprises about 0.1-90% of the dry weight of the enhanced ketogenic composition, such as about 1-50%, or about 5-25% of the dry weight of the composition. In a further embodiment, the mitochondria enhancing agent comprises about 10 mg-50 g of beetroot extract and preferably, about 50-5000 mg, or about 100-1000 mg.

Coenzyme Q10, also known as ubiquinone, ubidecarenone, coenzyme Q, CoQ10, CoQ, or Q10, may assume any one of three redox states for use in the present composition, namely, fully oxidized (ubiquinone), semi-oxidized (semiquinone or ubisemiquinone), and fully reduced (ubiquinol) forms, along with oxidized mitochondrially targeted forms of this enzyme (e.g. mitoquinone mesylate (MitoQ10)). As would be appreciated by one of skill in the art, coenzyme Q10 may be formulated in numerous ways to improve its bioavailability or effectiveness. Examples of such formulations for use in the present composition, which are not intended to be limiting, include the following: colloidal-based, solid dispersion-based, oily dispersion-based, micelle-based, nanoliposome-based, nanostructured lipid carrier-based, nanocrystal-based, nanoparticle-based, self-nanoemulsifiable-based, ascorbic acid with chelation-based and cyclodextrin complexation-based. In one embodiment, coenzyme Q10 comprises about 0.1-50% of the dry weight of the enhanced ketogenic composition, such as about 0.1-10%, or about 0.2-3% of the dry weight of the composition. In another embodiment, coenzyme Q10 comprises about 0.1-80% of the dry weight of the enhanced ketogenic composition, such as about 1-50%, or about 5-20% of the dry weight of the composition. In a further embodiment, the mitochondria enhancing agent comprises about 10 mg-1 g of coenzyme Q10 and preferably, about 30-900 mg, or about 50-400 mg.

Alpha lipoic acid suitable for use in the present composition may include, without limitation, alpha lipoic acid or its reduced form, dihydrolipoic acid, with R- and S-enantiomers either present individually, in racemic form or in any other mixture thereof. The R-enantiomer is produced naturally or synthetically, while the S-enantiomer is only produced synthetically and does not occur naturally. Additionally, any pharmaceutically acceptable salts or derivatives thereof are suitable for use in the present composition. Preferably, the alpha lipoic acid is present in racemic form. In one embodiment, the alpha lipoic acid comprises about 0.01-25% of the dry weight of the enhanced ketogenic composition, such as about 0.1-10%, or about 0.2-3% of the dry weight of the composition. In another embodiment, the alpha lipoic acid comprises about 0.01-90% of the dry weight of the enhanced ketogenic composition, such as about 5-50%, or about 10-30% of the dry weight of the composition. In another embodiment, the mitochondria enhancing agent comprises about 10 mg-3 g of alpha lipoic acid and preferably, about 25-900 mg, or about 50 mg-400 mg.

Creatine for use in the present composition may be in any suitable form, such as creatine monohydrate, creatine anhydrous, creatine citrate, creatine ascorbate, creatine ethyl ester, creatine nitrate, creatine magnesium chelate, creatine hydrochloride, creatine malate, creatine pyruvate, creatine phosphate, creatine citrate malate, creatine tartrate, creatine HMB (β-hydroxy β-methylbutyrate), effervescent creatine, creatine titrate, buffered creatine, micronized creatine and any combination thereof. Preferably, the creatine is creatine monohydrate. In one embodiment, creatine comprises about 0.1%-40% of the dry weight of the enhanced ketogenic composition, such as about 2-35%, or about 3-25% of the dry weight of the composition. In another embodiment, creatine comprises about 1%-40% of the dry weight of the enhanced ketogenic composition, such as about 20-70%, or about 30-50% of the dry weight of the composition. In another embodiment, the mitochondria enhancing agent comprises about 0.1-10 g of creatine and preferably, about 0.5-10 g or about 1-5 g.

Vitamin E for use in the present composition may be in the form of any one or more of the isomers thereof, including alpha-tocopherol, beta-tocopherol, gamma-tocopherol, delta-tocopherol, alpha-tocotrienol, beta-tocotrienol, gamma-tocotrienol, delta-tocotrienol, and stereoisomers thereof. Vitamin E may also be used in analogue form, including, for example, vitamin E esters (such as acetate, succinate or palmitate forms) or other forms of vitamin E which have been modified for improved stability or bioavailability. Preferably, the form of vitamin E used in the composition is alpha-tocopherol comprising biologically functional stereoisomers of alpha-tocopherol such as the naturally occurring RRR-configuration or the synthetically produced 2R-stereoisomer forms (RSR-, RRS-, and RSS-). In the most preferred embodiment, the vitamin E used is D (also known as RRR)-alpha tocopheryl acetate. In one embodiment, the vitamin E comprises about 0.01-25% of the dry weight of the enhanced ketogenic composition, such as about 0.1-10%, or about 0.2-3% of the dry weight of the composition. In another embodiment, the vitamin E comprises about 0.1-80% of the dry weight of the enhanced ketogenic composition, such as about 1-50%, or about 3-15% of the dry weight of the composition. In a further embodiment, the mitochondria enhancing agent comprises about 10 mg-1 g of vitamin E and preferably, about 25-900 mg or about 50-400 mg.

In one embodiment, the mitochondria enhancing agent comprises 100-1000 mg of beetroot extract, 50-400 mg of coenzyme Q10, 50 mg-400 mg alpha lipoic acid, 1-5 g of creatine and 50-400 mg of vitamin E.

In another embodiment, the mitochondria enhancing agent comprises 50-5000 mg of beetroot extract, 30-900 mg of coenzyme Q10, 25-900 mg alpha lipoic acid, 0.5-10 g of creatine and 25-900 mg of vitamin E.

The metabolic enhancing agent may comprise at least one weight loss agent. The weight loss agent may be selected from any suitable agent that promotes weight loss in an individual, e.g. by at least about 0.5%, and preferably a body weight reduction of about 1% or more, e.g. by 5%, 10%, 30%, 50%, 70% or greater of the body weight of the individual prior to treatment with the present composition, or a reduction in the rate of rising body weight by at least about 1% or more, and preferably a reduction of about 5% or more, e.g. by 10%, 30%, 50%, 70%, 90% or greater to the rate of body weight increase prior to treatment. Suitable weight loss agents may promote weight loss by any one or more of several mechanisms including, but not limited to, the following: decreasing food intake or promoting satiety, decreasing lipid absorption, increasing energy expenditure, decreasing pre-adipocyte differentiation and proliferation, decreasing lipogenesis and/or increasing lipolysis. Examples of weight loss agents include, but are not limited to, chitosan, psyllium, guar gum, capsaicin, caffeine, *Garcina cambogia, Pinus densiflora*, capsaicin, yohimbe, hoodia, glucomannan, African mango, guarana, pyruvate, carnitine, beta-glucans, fucoxanthin, raspberry ketone, white kidney bean, kola nut, chromium, ginseng, psyllium, St. John's wort, dandelion, hydroxycitric acid, conjugated linoleic acid, green tea extract, black tea extract, green coffee bean extract, forskolin, bitter orange and mixtures thereof.

In one embodiment, caffeine is present in the weight loss agent, either as anhydrous caffeine or within a naturally occurring source such as green tea or green coffee beans. The anhydrous caffeine may be derived from any suitable source, such as from any one of about 60 plant species naturally containing caffeine, which include tea leaves, coffee beans, cocoa beans, yerba maté, guarana berries, guayusa, and the yaupon holly. Preferably, the weight loss agent comprises a daily dose of approximately 25-1000 mg of caffeine, such as about 100-250 mg.

In another embodiment, the weight loss agent is substantially caffeine-free. In the substantially caffeine-free weight loss agent, ingredients which naturally contain caffeine may be provided in decaffeinated form, such that each decaffeinated ingredient contains less than 1% of caffeine by dry weight for example. Methods for decaffeination are known in the art.

In one embodiment, the weight loss agent comprises a mixture of green tea extract, black tea extract, green coffee bean extract, conjugated linoleic acid and forskolin.

In another embodiment, the weight loss agent comprises a mixture of green tea extract, green coffee bean extract and forskolin.

The green tea extract for use in the present composition may be selected from any suitable green tea leaf or green tea source such as Sencha, Fukamushi Sencha, Gyokuro, Kabusecha, Matcha, Tencha, Genmaicha, Matcha, Shincha, Hojicha, Ichibanchagreen, Nibancha and Sanbancha tea, which are derived from the *Camellia sinensis* leaf. Green tea is abundant in polyphenols such as catechins. Examples of such catechins include epigallocatechin gallate, catechin, catechin gallate, epicatechin, gallocatechin, epigallocatechin, and epicatechin gallate. Preferably, the green tea extract contains 10% or more of catechins by dry weight, with about 50% or more of the catechins being epigallocatechin gallate. Green tea extract for use in the present composition may be either caffeinated or substantially decaffeinated, for example, having less than 1% of caffeine by dry weight. Preferably, the green tea extract contains 30% caffeine by dry weight and 20% catechins by dry weight. In one embodiment, the enhanced ketogenic composition comprises about 0.01-25% green tea extract by wt of the dry weight thereof, such as about 0.1-10%, or about 1-2.5% of the dry weight of the composition. In another embodiment, the green tea extract comprises about 0.1-90% of the dry weight of the enhanced ketogenic composition, such as about 5-50%, or about 10-30% of the dry weight of the composition. In another embodiment, the weight loss agent comprises a daily dosage of about 10 mg-5 g of green tea extract and preferably, about 25-1000 mg or about 50-500 mg.

The black tea extract for use in the present composition may be obtained from any suitable black tea leaf or black tea source including unblended black tea sources such as Congou, Assam, Darjeeling, Nilgiri or Ceylon or blended black teas such as Earl Grey, English Breakfast tea, English afternoon tea, Irish breakfast tea or Masala chai, which are derived from the *Camilla sinensis* leaf. Black tea is abundant in polyphenols such as theaflavins, thearubigins and catechins. Examples of theaflavins include theaflavin, theaflavin-3-gallate, theaflavin-3'-gallate and theaflavin-3,3'-gallate. Preferably, the black tea extract for use in the present composition comprises 10% or more of polyphenols by dry weight. Black tea extract for use in the present composition may be either caffeinated or substantially decaffeinated, for example, having less than 1% of caffeine by dry weight. Preferably, the black tea extract comprises at least about 30% polyphenols by dry weight. In one embodiment, the black tea extract comprises about 0.01-25% of the dry weight of the enhanced ketogenic composition, such as about 0.1-10%, or about 1-2.5% of the dry weight of the composition. In another embodiment, the black tea extract comprises about 0.1-80% of the dry weight of the enhanced ketogenic composition, such as about 5-50%, or about 10-30% of the dry weight of the composition. In another embodiment, the weight loss agent comprises a daily dosage of about 10 mg-5 g of black tea extract and preferably, about 25-750 mg or about 50-500 mg.

The green coffee bean extract for use in the present composition may be selected from any suitable green coffee bean source such as *Coffea Arabica* or *Coffea canephora*. Green coffee beans contain several types of chlorogenic acids, such as 3-caffeoylquinic acid, 4-caffeoylquinic acid and 5-caffeoylquinic acid. Preferably, the green coffee bean extract for use in the present composition comprises about comprises about 30% or more of chlorogenic acids by dry weight. Green coffee bean extract for use in the present composition may be either caffeinated or substantially decaffeinated, for example, having less than 1% of caffeine by dry weight. Preferably, the green coffee bean extract contains at least 30% chlorogenic acids and at least 35% caffeine by dry weight. Green coffee bean extract for use in the present composition may be either caffeinated or substantially decaffeinated, for example, having less than 1% of caffeine by dry weight. In one embodiment, the green coffee bean extract comprises about 0.01-25% of the dry weight of the enhanced ketogenic composition such as about 0.1-10%, or about 1-2.5% of the dry weight of the composition. In another embodiment, the green coffee bean extract comprises about 0.1-80% of the dry weight of the enhanced ketogenic composition such as about 5-50%, or about 10-30% of the dry weight of the composition. In another embodiment, the weight loss agent comprises a daily dosage of about 10 mg-5 g of green coffee bean extract and preferably, about 25-1000 mg or about 50-500 mg.

The conjugated linoleic acid for use in the present application may be obtained from any suitable source such as safflower oil, sunflower oil or grass-fed beef sources. As used herein, the term "conjugated linoleic acid" refers to any of the at least 28 known geometric or positional isomers of linoleic acid, wherein two of the double bonds of the molecule are conjugated such as in the cis-9:trans-11 or trans-10:cis-12 form. The composition may include a single isomer, a mixture of isomers, natural isomers, synthetic isomers, or a pharmaceutically acceptable salt, ester, monoglyceride, diglyceride, triglyceride, metabolic precursor thereof, or any combinations thereof. Preferably, the conjugated linoleic acid contains about a 50:50 mixture of its cis-9:trans-11, and trans-10:cis-12 isomers. In one embodiment, the conjugated linoleic acid source comprises about 0.1%-40% of the dry weight of the enhanced ketogenic composition composition, such as about 10-35%, or about 15-25% of the dry weight of the composition. In another embodiment, the conjugated linoleic acid comprises about 0.1-80% of the dry weight of the enhanced ketogenic composition such as about 20-70%, or about 30-50% of the dry weight of the composition. In another embodiment, the weight loss agent comprises a daily dosage of about 10 mg-10 g of conjugated linoleic acid and preferably, about 500 mg-3 g.

The forskolin for use in the present composition may be obtained from any suitable source. Forskolin may be extracted from the *Coleus forskohli* plant, or synthetically produced. Preferably, the forskolin extract is derived from the *Coleus forskohli* plant and is standardized to comprise about 40% forskolin. In one embodiment, forskolin comprises about 0.025-5% of the dry weight of the enhanced ketogenic composition such as about 0.01-2.5%, or about 0.1-0.5% of the dry weight of the composition. In another embodiment, the forskolin comprises about 0.05-50% of the dry weight of the enhanced ketogenic composition such as about 0.1-30%, or about 0.5-10% of the dry weight of the composition. In another embodiment, the weight loss agent comprises a daily dosage of about 1 mg-200 mg of forskolin and preferably, about 1-100 mg or about 15 mg-50 mg.

In one embodiment, the weight loss agent comprises 25-1000 mg green tea extract, 25-1000 mg green coffee bean extract and 1-100 mg forskolin.

In another embodiment, the weight loss agent comprises 50-500 mg green tea extract, 50-500 mg green coffee bean extract and 15 mg-50 mg forskolin.

The metabolic enhancing agent may comprise at least one muscle mass preservation agent. The muscle mass preservation agent may be selected from any suitable agent that promotes the maintenance of muscle mass in an individual. For example, the muscle mass preservation agent may comprise beta-hydroxy-beta-methylbutyrate (HMB), ketoisocaproate, suitable protein sources, protein precursors or derivatives thereof, and any combination thereof.

HMB for use in the present composition may be in any suitable form, such as in the free acid, salt, ester or lactone form and any combination thereof. Preferably, the HMB is in the free acid form or the calcium salt form as calcium HMB monohydrate. In one embodiment, HMB comprises about 0.1%-40% of the dry weight of the enhanced ketogenic composition, such as about 2-35%, or about 3-25% of the dry weight of the composition. In another embodiment, the muscle mass preservation agent comprises a daily dosage of about 0.5-25 g of HMB and preferably, about 1-3 g.

The metabolic enhancing agent may comprise at least one nitric oxide precursor. The nitric oxide precursor may be selected from any suitable agent which possesses the characteristic of promoting vasodilation and/or inhibiting vasoconstriction in an individual. For example, the nitric oxide precursor may comprise citrulline, arginine, nitrate, nitrite and any physiologically acceptable precursors, derivatives, salts and any combination thereof. Examples of suitable precursors of arginine include ornithine, glutamine and glutamate.

Citrulline for use in the present composition may be in any suitable form, such as physiologically acceptable salts, derivates, precursors or any combination thereof. Preferably, the citrulline is in the L-citrulline form. In one embodiment, citrulline comprises about 0.1%-40% of the dry weight of the enhanced ketogenic composition, such as about 2-35%, or about 3-25% of the dry weight of the composition. In another embodiment, the nitric oxide precursor comprises a daily dosage of about 0.5-25 g of citrulline and preferably, about 1-4 g.

In one embodiment, the enhanced ketogenic composition comprises a ketogenic agent in a daily dosage sufficient to result in blood ketone body concentrations of 0.1 mM to about 25 mM, as the weight loss agent a mixture comprising a daily dosage of 50-1000 mg of green tea extract, 50-1000 mg of green coffee bean extract, 15-100 mg of forskolin, as the mitochondria enhancing agent is comprising a mixture comprising a daily dosage of 50-5000 mg of beetroot extract, 50-900 mg of coenzyme Q10, 50-900 mg alpha lipoic acid and 50-900 mg of vitamin E, as the muscle mass preservation agent 0.5-25 g of HMB and as the nitric oxide precursor 0.5-25 g of citrulline.

In another embodiment, the enhanced ketogenic composition comprises a ketogenic agent in a daily dosage sufficient to result in blood ketone body concentrations of 0.1 mM to about 25 mM, as the weight loss agent a mixture comprising a daily dosage of 50-500 mg of green tea extract, 50-500 mg of black tea extract, 50-500 mg of green coffee bean extract, 500 mg-3 g of conjugated linoleic acid and 15 mg-50 mg of forskolin, and as the mitochondria enhancing agent a mixture comprising a daily dosage of 100-1000 mg of beetroot extract, 50-200 mg of coenzyme Q10, 50 mg-500 mg alpha lipoic acid, 1-5 g of creatine and 50-200 mg of vitamin E, as the muscle mass preservation agent 0.5-25 g of HMB and as the nitric oxide precursor 0.5-25 g of citrulline.

In a further embodiment, the enhanced ketogenic composition comprises a ketogenic agent in a daily dosage sufficient to result in blood ketone body concentrations of 0.1 mM to about 25 mM, as the mitochondria enhancing agent a mixture comprising a daily dosage of 50-5000 mg of beetroot extract, 50-900 mg of coenzyme Q10, 50-900 mg alpha lipoic acid and 50-900 mg of vitamin E, as the muscle mass preservation agent 0.5-25 g of HMB and as the nitric oxide precursor 0.5-25 g of citrulline.

According to one embodiment, the ketogenic agent or enhanced ketogenic composition may be used as a sole, primary, or supplemental source of nutrition. Where the ketogenic agent or enhanced ketogenic composition is used as a sole source of nutrition, the composition will generally comprise other essential nutrients required in an adequate diet, such as vitamins, minerals, proteins, carbohydrates, fibre, and fats/lipids as would be appreciated by one of skill in the art.

Where the ketogenic agent or enhanced ketogenic composition is used as other than a sole source of nutrition, it may be formulated with at least one additional source of nutrition, including, but not limited to; proteins, carbohydrates, lipids, fibre, vitamins, minerals, antioxidants, prebiotics, probiotics, phytochemicals or phytonutrients.

Proteins suitable for inclusion in the ketogenic agent or enhanced ketogenic composition include any food-grade protein which is suitable for oral administration to an individual. Suitable proteins may be selected from any suitable protein source, including those from an animal source, a dairy source, a plant source, an insect source or any combination thereof. Non-limiting examples of insect sources of protein include: cricket protein, grasshopper protein, mealworm protein, earthworm protein and any combination thereof. Non-limiting examples of animal sources of protein include: cow protein, pig protein, goat protein, lamb protein, poultry protein (such as chicken, duck, goose, pheasant and the like), wild game protein, seafood protein (such as fish and shellfish) and any combination thereof. Non-limiting examples of dairy sources of protein include: whey protein, whey protein concentrate, whey protein isolate, milk protein concentrate, milk protein isolate, powdered fat and/or fat-free milk, micellar casein, acid casein, potassium caseinate, calcium caseinate, sodium caseinate and any combination thereof. Non-limiting examples of plant sources of protein include: pea protein, yeast protein, soy protein, corn protein, wheat protein, rice protein, canola protein, peanut protein, bean protein, lentil protein, and any combination thereof. The protein source may be non-hydrolyzed, partially hydrolyzed or hydrolyzed and may be in the form of an intact protein, amino acid or peptide. Non-limiting examples of amino acids may include essential amino acids such as: leucine, isoleucine, valine, tryptophan, methionine, threonine, phenylalanine and lysine and semi-essential amino acids such as: histidine and arginine and non-essential amino acids such as tyrosine, aspartic acid, glycine, alanine, cysteine, arginine, glutamic acid, proline, glutamine, serine, asparagine, taurine and any combination thereof. Preferably, the protein source is a high-quality protein source, at least comprising each of the essential amino acids. More preferably, the protein source is a high-quality protein source containing an additional amount of leucine. In one embodiment, the present composition may include about 0.1-99% by wt protein. Proteins may be included in the composition in an amount that does not adversely affect the function of the composition.

Carbohydrates suitable for inclusion in the ketogenic agent or enhanced ketogenic composition include any food-grade carbohydrate which is suitable for oral administration to an individual. Suitable carbohydrates include the following non-limiting examples: quickly-digestible carbohydrates such as monosaccharides, disaccharides or polysaccharides (e.g. glucose, fructose, sucrose, dextrose, maltodextrin and maltose), molasses, honey, maple syrup, corn syrup, high fructose corn syrup, sugar alcohols (e.g. xylitol, maltitol, erythritol, sorbitol, hydrogenated starch hydrolysates, isomalt and mannitol) or more slowly-digestible carbohydrates such as katakuri starch, cornstarch, potato starch, arrowroot, alginin, xanthan gum, locust bean gum, oat bran, wheat bran and rice bran, or combinations thereof. In one embodiment, the present composition may include about 0.1-99% by wt carbohydrates. Carbohydrates may be included in the composition in an amount that does not adversely affect the function of the composition.

The ketogenic agent or enhanced ketogenic composition may comprise any food-grade source of fibre which is suitable for oral administration to an individual. Suitable sources of fibre include the following non-limiting examples: water-soluble dietary fiber such as beta-glucans, pectin, xylose, plant gums, inulin and alginates, and insoluble dietary fiber such as lignin, beta-glucans, xanthan gum, resistant starches and combinations thereof. Fibre may be included in the composition in an amount that does not adversely affect the function of the composition.

The ketogenic agent or enhanced ketogenic composition may comprise any food-grade source of lipids suitable for oral administration to an individual. Suitable sources of lipids include the following non-limiting examples: olive oil, safflower oil, canola oil, coconut oil, corn oil, palm oil, palm kernel oil, soybean oil, peanut oil, fish oil, almond oil, sunflower oil, butter, lard, and sources of medium chain triglycerides, long chain triglycerides, monoglycerides, diglycerides, cold water fish (e.g. cod, salmon, tuna, sardines, mackerel, krill and squid), algae, dark leafy green vegetables, plant and plant seed oils (e.g. flaxseed oil, canola oil and walnut oil), nuts (e.g. walnuts) and combinations thereof. Lipids may be included in the composition in an amount that does not adversely affect the function of the composition.

The ketogenic agent or enhanced ketogenic composition may comprise any food-grade source of vitamins and minerals which are suitable for oral administration to an individual. Suitable vitamins include the following non-limiting examples: vitamin A, vitamin C, vitamin D, vitamin K, thiamine, riboflavin, niacin, pantothenic acid, pyridoxine, folic acid, cobalamin, biotin, carotenoids (e.g. lutein, beta-carotene, lycopene and cryptoxanthin), choline, inositol and combinations thereof, and suitable minerals include, but are not limited to, calcium, phosphorus, selenium, chromium, zinc, molybdenum, iodine, chloride, phosphorus, manganese, fluoride, potassium, iron, copper, magnesium, sodium and combinations thereof. Vitamins may be included in an amount that complies with recommended daily dosages, either alone or in combination with diet. Vitamins and minerals may be included in the composition in an amount that does not adversely affect the function of the composition.

The ketogenic agent or enhanced ketogenic composition may comprise any food-grade source of antioxidants which are suitable for oral administration to an individual. Suitable antioxidants include the following non-limiting examples: citric acid monohydrate, vitamin A, vitamin C, folic acid, and beta-carotene, iron, copper, butylated hydroxyamisole, butylated hydroxytoluene, propyl gallate, tertiary butylhydroquinone, resveratrol, and plant phytonutrients or phytochemicals (e.g. flavonoids and lignin). Herbs or herbal extracts (e.g. oregano, Goji berry, dill, garden thyme, rosemary and peppermint), tea leaves or tea leaf extracts (e.g. *Camellia sinensis*), coffee bean extracts (e.g. *Coffea canephora* and *Coffea arabica*), brewed coffee or tea or brewed coffee or tea extracts (e.g. oolong tea and *Coffea robusta*) and other plants or plant extracts (e.g. ginger root) may also be used as a source of antioxidants, as well as combinations of any of the antioxidants. Antioxidants may be included in the composition in an amount that does not adversely affect the function of the composition.

The ketogenic agent or enhanced ketogenic composition may comprise any food-grade source of prebiotics which are suitable for oral administration to an individual. Suitable prebiotics include the following non-limiting examples: dietary fibers and carbohydrate polymers such as cellulose, inulin, gums, trans-galactooligosaccharide, fructans, resistant starches, xylooligosaccharides, hemicelluloses, pectin, sugar alcohols, beta-glucans and combinations thereof.

The ketogenic agent or enhanced ketogenic composition may comprise any food-grade source of probiotics which are suitable for oral administration to an individual. Suitable probiotics include the following non-limiting examples: *Lactobacillus Acidophilus, Lactobacillus reuteri, Lactobacillus rhamnosus, Lactobacillus gasseri, Lactobacillus salivarius, Lactobacillus bulgaricus, Lactobacillus helventicus, Lactobacillus silivarus, Lactobacillus plantarum, Lactobacillus casei, Lactobacillus paracassei, Lactobacillus fermentum, Bifidobacterium breve, Bifidobacterium lactis, Bifidobacterium longum, Bifidobacterium bifidum, Bifidobacterium infantis, Bifidobacterium bifidum, Bacillus coagulans, Saccharomyces boulardii, Pediococcus acidlacti* and combinations thereof.

The ketogenic agent or enhanced ketogenic composition may comprise any food-grade source of phytochemicals or phytonutrients which are suitable for oral administration to an individual. Suitable phytochemicals or phytonutrients include the following non-limiting examples: phytosterols including sterols (e.g. cempesterol) and stanol (e.g. sitostanol), soy flavonoids (e.g. genistein and glycitein), garlic and organosulfur compounds (e.g. L-cysteine sulfoxides and γ-glutamyl-L-cysteine peptides), carotenoids (e.g. zeaxanthin alpha-carotene, beta-carotene, lycopene, beta-cryptoxanthin and lutein), resveratrol, curcumin, fiber (e.g. lignin and cellulose), indole 3-carbinol and condensation products (e.g. 3,3'-diindolylmethane and 5,11-dihydroindolo-[3,2-b]carbazole), chlorophyll and chlorophyllin isothiocyanates, isothiocyanates (e.g. sulforaphane and benzyl isothiocyanate) and combinations thereof.

Prebiotics, probiotics, phytochemicals and phytonutrients may be included in the composition in an amount that does not adversely affect the function of the composition.

The present composition may additionally include at least one physiologically acceptable excipient. The term "physiologically acceptable" is used herein to refer to excipients which are food-grade and thus, acceptable for consumption or administration to a mammal. Examples of suitable excipients, which are not to be construed as limiting, include flavouring agents, sweetening agents, anti-caking agents/flowing agents, emulsifiers, stabilizers, masking agents, colorants, preservatives, disintegrants, binders, thickeners and pH adjusters.

Non-limiting examples of flavouring agents include natural or artificial flavours such as fruit flavours (e.g. raspberry, orange, apple, pomegranate, mixed berry, lemon, lime, watermelon, strawberry, blueberry, pineapple, coconut, grape, cherry, banana, peach, mango, kiwifruit, cranberry), sodium sources (e.g. sodium chloride and monosodium glutamate), high fructose corn syrup, vanilla, chocolate, unsweetened chocolate, honey, molasses, brown sugar, coffee, cocoa, mint, maple, almond, or extracts or combinations thereof. Savoury flavourings may also be used (e.g. beef, chicken or vegetable flavourings).

Non-limiting examples of sweetening agents include natural sweeteners such as, glucose, fructose, sucrose, dextrose, maltose, brown sugar, molasses, honey, maple syrup, corn syrup, high fructose corn syrup, erythritol, xylitol, sorbitol, isomalt, monatin, monellin, curculin, brazzein, tagatose and mannitol, and artificial sweeteners such as aspartame, acesulfame K, saccharin cyclamate and sucralose.

Non-limiting examples of further excipients include: anticaking agents or flowing agents such as silicates (e.g. silicon dioxide) and calcium or magnesium stearates; emulsifiers such as agar, gums, egg yok, lecithin, monostearate, monosodium phosphate, monoglycerides, diglycerides and alginates; stabilizers such as glycerine, agar, gums, alginates and pectin; masking agents such as glycerine, sodium chloride, peppermint, lemon-lime, mint, cherry, black liquorice, peach, apricot, raspberry, or sweetening agents such as aspartame or sucrose; colorants such as those which are suitable for inclusion in foods, e.g. FD&C blue #1, FD&C blue #2, FD&C citrus red #2, FD&C green #3, FD&C red #3, FD&C red #40, FD&C yellow #5 and FD&C yellow #6; preservatives such as butylated hydroxyanisole, butylated hydroxytoluene, ethylenediaminetetraacetic acid, nitrates (e.g. sodium nitrate), sulfites (sodium bisulfite), benzoates (sodium benzoate), sorbates (e.g. sodium sorbate) and sodium chloride; disintegrants such as starches (e.g. potato starch), alginic acid, cellulose and derivatives thereof, and calcium silicate; binders such as stearic acid, gelatin, saccharides and derivatives thereof, sugar alcohols, polyethylene glycol and cellulose; thickeners such as polysaccharide-based thickeners such as vegetable gums, pectin and starches or protein-based thickeners such as gelatin, egg white and collagen; and pH adjusters such as citric acid, ammonium carbonate, ammonium phosphate, calcium carbonate, sodium hydroxide, malic acid and phosphoric acid. As will be appreciated by one of skill in the art, for each type of excipient (e.g. flavouring agent, sweetener, emulsifier, preservative, etc.), a single excipient may be used, or a combination of two or more may be used.

The ketogenic agent or enhanced ketogenic composition may be formulated for oral administration including, for example, solid, semi-solid, liquid, semi-liquid, powder, suspension, emulsion, solution, ready-to-drink beverage, gel, bar, pill, tablet or capsule form. The term "oral" or "orally" as used herein is intended to include any method in which the ketogenic agent or enhanced ketogenic composition is introduced into the digestive tract including the stomach and small intestine. Examples of oral administration may include administration via mouth, directly into the stomach using a feeding tube, through the nose to the stomach via a feeding tube and through the nose to the small intestine via a feeding tube. In a preferred embodiment, the ketogenic agent is provided as a liquid, powder or gel, while the mitochondria enhancing agent, weight loss agent, muscle mass preservation agent and nitric oxide precursor are provided as a liquid, powder or bar form. In a preferred embodiment, the metabolic enhancing composition is provided as a loose powder, a bar or in capsules. The loose powdered composition may be reconstituted in water or any suitable liquid (such as juice, milk, saline, etc.) immediately prior to consumption. When provided in loose powdered form, the metabolic enhancing composition may be packaged in individual use containers, packets or sachets, or in larger bulk containers. When provided as a powder in capsules, any suitable capsule may be used including gelatin and hard hydroxypropyl methylcellulose (also known as Hypromellose) capsules.

The ketogenic agent or enhanced ketogenic composition may also be administered parenterally, either alone or in combination with at least one pharmaceutically acceptable adjuvant, for use in methods in accordance with embodiments of the invention. The expression "pharmaceutically acceptable" means acceptable for use in the pharmaceutical and veterinary arts, i.e. not being unacceptably toxic or otherwise unsuitable. Examples of pharmaceutically acceptable adjuvants include diluents, excipients and the like. Reference may be made to "Remington's: The Science and Practice of Pharmacy", 21st Ed., Lippincott Williams & Wilkins, 2005, for guidance on drug formulations generally. The selection of adjuvant depends on the intended mode of administration of the composition. In one embodiment of the invention, the composition is formulated for administration by infusion, or by injection either subcutaneously or intravenously. The composition may be prepared as an aqueous solution in sterile and pyrogen-free form and optionally buffered or made isotonic. Thus, the composition may be administered in distilled water or, more desirably, in saline, phosphate-buffered saline or 5% dextrose solution. Creams, lotions and ointments may be prepared for topical application using an appropriate base such as a triglyceride base. Such creams, lotions and ointments may also contain a surface active agent. Aerosol formulations may also be prepared in which suitable propellant adjuvants are used. Other adjuvants may also be added to the composition regardless of how it is to be administered for example, anti-microbial agents may be added to the composition to prevent microbial growth over prolonged storage periods.

The composition may include a coating or may be encased in a protective material to prevent undesirable degradation thereof by enzymes, acids or by other conditions that may affect the therapeutic activity thereof.

The present method and composition are useful to improve at least one of muscle function, autophagic activity and mitochondrial capacity in an individual having a lysosomal storage disease. The term "individual" is used herein to refer to a mammal, preferably a human. The method comprises administering to the individual an effective amount of the ketogenic agent or enhanced ketogenic composition. The term "improve" is used herein with respect to the variables of muscle function and autophagic activity, to refer to a healthy increase in the variables, i.e. an increase in the variables that is considered to promote health and reduce the adverse effects from a lysosomal storage disease.

As used herein, the term "muscle" refers to skeletal muscles and non-skeletal muscles which may be consciously controlled such as the diaphragm muscles. The term "muscle function" refers to the ability of muscles to produce force and motion. Muscle function may be measured by numerous methods, such as a 1-repetition max (1-RM) test or a grip strength test which primarily test muscle force production, or by tests which emphasize both force and motion production ability such as callisthenic-type exercise tests (e.g. burpees), a 6-second walk test or a rotarod balance test. Improved muscle function refers to an increase in the amount of muscle function in an individual by at least about 0.5%, and preferably an increase of about 1% or more, e.g. by 5%, 10%, 30%, 50%, 70% or greater from the muscle function of the individual prior to treatment with the present composition, or at least a reduction in the rate of muscle function loss in an individual who is losing muscle function by at least about 1% or more, and preferably a reduction in the rate of muscle function loss by about 5% or more, e.g. by 10%, 30%, 50%, 70%, 90% or greater from the rate of muscle function loss in the individual prior to treatment with the present composition.

As used herein, the term autophagy includes chaperone mediated autophagy, microautophagy, macroautophagy and other cellular protein degradation systems which are integrated with the aforementioned autophagy systems, such as the ubiquitin proteasome system. The term "autophagic activity" refers the amount or rate of autophagic flux occurring in a cell at a given time. Important indicators of autophagic flux include the following non-limiting examples: the amount of autophagic intermediates which are known to tag proteins for degradation such as p62 or ubiquitin, the rate of autophagosome formation, the rate of autophagosome delivery to the lysosome and the rate of clearance or degradation of organelles, glycogen and other macromolecules within the lysosome. Improved autophagic activity refers to an increase in the amount of autophagic activity in an individual by at least about 0.5%, and preferably an increase of about 1% or more, e.g. by 5%, 10%, 30%, 50%, 70% or greater from the autophagic activity of the individual prior to treatment with the present composition, or at least a reduction in the rate of autophagic activity loss in an individual who is experiencing a lowering of autophagic activity by at least about 1% or more, and preferably a reduction in the rate of autophagic activity loss by about 5% or more, e.g. by 10%, 30%, 50%, 70%, 90% or greater from the rate of autophagic activity loss in the individual prior to treatment with the present composition.

As used herein, the term "mitochondrial capacity" refers to the total physiological productive capacity for mitochondria to produce cellular energy stores by carrying out cellular respiration. The term encompasses the mitochondrial capacity of one or more mitochondria and may be used to refer to the mitochondrial capacity of mitochondria within specific regions (such as specific muscles or organs) or within the entire body. Important indicators of mitochondrial capacity include the following non-limiting examples: an increase in the enzymatic capacity expressed in absolute terms or relative to the total number of mitochondria measured, the presence of biomarkers of mitochondrial integrity, such as the absence of deletions, cristae fragmentation or pleomorphism and a heightened amount (but not an excessive amount) of mitochondrial turnover via mitophagy or mitochondrial fission and fusion events. For example, improved mitochondrial capacity refers to an increase in relative mitochondrial enzymatic activity in an individual by at least about 0.5%, and preferably an increase of about 1% or more, e.g. by 5%, 10%, 30%, 50%, 70% or greater from the relative mitochondrial enzymatic activity of the individual prior to treatment with the present composition, or at least a reduction in the rate of relative mitochondrial enzymatic activity decline in an individual who is experiencing a decrease in relative mitochondrial enzymatic activity by at least about 1% or more, and preferably a reduction in the rate of mitochondrial capacity loss by about 5% or more, e.g. by 10%, 30%, 50%, 70%, 90% or greater from the rate of relative mitochondrial enzymatic activity decline in the individual prior to treatment with the present composition. Improved mitochondrial capacity may also refer to a normalization of mitochondrial capacity in one or more tissues within the levels of a healthy individual, such as the normalization of the accumulation of mitochondrial content having a lower relative capacity (activity/total mitochondrial content) in one or more tissues within the levels of a healthy individual occurring in response to a pathogenic process (i.e., lysosomal storage disease, oxidative stress, impaired autophagy).

The ketogenic agent or enhanced ketogenic composition may be administered in a daily therapeutically effective amount to a mammal in need thereof, one or more times per day, for a period ranging from one day to chronic or long-term administration. The term "mammal" is used herein to refer to human and non-human mammals such as domestic animals (cats, dogs, horses and other livestock). The term "daily effective amount" as used herein, refers to an amount which achieves the effects desired in the mammal, without surpassing any amount which may cause undesirable side effects. For example, a daily effective amount of the ketogenic agent or enhanced ketogenic composition may be administered once per day, or a daily effective amount of the ketogenic agent or enhanced ketogenic composition may be divided into 2, 3, 4, 5, 6 or more portions to be administered throughout the day. In one embodiment, the ketogenic agent or enhanced ketogenic composition is administered once a day to an individual in the morning when first waking up. The ketogenic agent or enhanced ketogenic composition may also be administered to an individual in the morning and then administered again prior to the individual retiring to bed. The ketogenic agent or enhanced ketogenic composition may be administered to an individual in need thereof for 1, 2, 3, 4, 5, 6 or 7 days in a week and for 1, 2, 3, 4, 5, 6, 7, 8, 9, 10 or more weeks. In one embodiment, the ketogenic agent or enhanced ketogenic composition is administered chronically to an individual in need thereof. The term "chronically" as used herein refers to the administration of the ketogenic agent or enhanced ketogenic composition for a period of at least 2-4 or more months, for example, administration of the ketogenic agent or enhanced ketogenic composition on a continual basis beyond 6 months, at a frequency of at least 2 or more days/week.

In one embodiment, the ketogenic agent or enhanced ketogenic composition may be administered in conjunction with an additional therapy for the lysosomal storage disease. For example, the ketogenic agent may be administered to an individual with Pompe disease who is being treated with a molecular chaperone therapy such as Duvoglustat HCL/AT2220/1-deoxynojirimycin/DNJ or Miglustat. Other examples of molecular chaperone therapies which could be administered in conjunction with the ketogenic agent or enhanced ketogenic composition include galactose or HCL/AT1001/1-deoxygalactonojirimycin/DGJ for individuals with Fabry disease, Afegostat tartrate/AT2101/isofagomine/IFG or Ambroxol for individuals with Gaucher, type I disease, NOEV for individuals with GM1 gangliosidosis disease, N-acetylglucosamine thiazoline/NGT, AdNDJ/OT1001 or Pyrimethamine for individuals with GM2 gangliosidosis disease, glucosamine for individuals with MPS BIC disease and CS38 for individuals with Batten disease. For another example, the ketogenic agent or enhanced ketogenic composition may be administered in conjunction with enzyme replacement therapies such as the following non-limiting examples such as agalsidase beta for individuals with Fabry disease, imiglucerase, velaglucerase alfa or taliglucerase for individuals with Type 1 Gaucher disease, alglucosidase alfa for individuals with Pompe Disease, laronidase for individuals with MPS I, idursulfase for individuals with MPS II or galsulfase for individuals with MPS VI. Elosulfase alfa for individuals with MPS IVa.

The components of the composition may be administered in conjunction, either together, in a single composition, or individually in separate dosage forms which may be the same or at different times. For example, the ketogenic agent may be administered in liquid form, while the metabolic enhancing agent may be administered separately in a different administrable dosage form, such as a capsule during the day at the same time as the ketogenic agent is administered, or at a different time, and at the same frequency or at a different frequency. For example, the liquid may be administered three times daily, while the capsules are administered once or twice a day.

A method and composition are provided which are useful for the treatment of lysosomal storage disease in an individual. Examples of lysosomal storage diseases that may be treated using the present method and composition are set out in Table 1 below.

TABLE 1

Alpha-mannosidosis
Aspartylglucosaminuria
Cholesteryl Ester Storage Disease
Cystinosis
Danon Disease
Fabry Disease
Farber Disease
Fucosidosis
Galactosialidosis
Gaucher Disease - Type I
Gaucher Disease - Type II
Gaucher Disease - Type III
GM1 - Gangliosidosis (types I, II, III)
GM2 - Sandhoff disease (I/J/A)
GM2 - Tay-Sachs disease
GM2 - Gangliosidosis, AB variant
I-Cell Disease/Mucolipidosis II
Krabbe Disease
Lysosomal acid lipase deficiency TABLE 1-continued Metachromatic Leukodystrophy
MPS I - Hurler Syndrome
MPS I - Scheie Syndrome
MPS I Hurler-Scheie Syndrome
MPS II - Hunter Syndrome
MPS IIIA - Sanfilippo Syndrome Type A
MPS IIIB - Sanfilippo Syndrome Type B
MPS IIIC - Sanfilippo Syndrome Type C
MPS IIID - Sanfilippo Syndrome Type D
MPS IV - Morquio Type A
MPS IV - Morquio Type B
MPS IX - Hyaluronidase Deficiency
MPS VI - Maroteaux-Lamy
MPS VII - Sly Syndrome
Mucolipidosis I - Sialidosis
Mucolipidosis IIIC
Mucolipidosis Type IV
Multiple Sulfatase Deficiency
Neuronal Ceroid Lipofuscinosis T1
Neuronal Ceroid Lipofuscinosis T2
Neuronal Ceroid Lipofuscinosis T3
Neuronal Ceroid Lipofuscinosis T4
Neuronal Ceroid Lipofuscinosis T5
Neuronal Ceroid Lipofuscinosis T6
Neuronal Ceroid Lipofuscinosis T7
Neuronal Ceroid Lipofuscinosis T8
Niemann-Pick Disease Type A
Niemann-Pick Disease Type B
Niemann-Pick Disease Type C
Pompe Disease
Pycnodysostosis
Salla Disease
Schindler Disease
Wolman Disease Embodiments of the invention are described by reference to the following specific examples which are not to be construed as limiting.

EXAMPLES

Example 1—Effect of the Ketogenic Agent and Enhanced Ketogenic Composition on Muscle Function, Autophagic Activity and Mitochondrial Capacity in Mice Having a Lysosomal Storage Disease To determine if the ketogenic agent and enhanced ketogenic composition could improve autophagic activity, muscle function and mitochondrial capacity in mice having a lysosomal storage disease, mice lacking the acid alpha glucosidase (GAA) protein (an established mouse model of Pompe disease) were administered the ketogenic agent, the enhanced ketogenic composition or one of several control diets for a period of 8 weeks.

Breeding of GAA mice. Four GAA heterozygous breeding pairs (HET; GAA−/+; 6neo/6+) were obtained from Jackson Laboratories (Maine, USA) to generate homozygous GAA knock-outs (GAA; GAA−/−; 6neo/6neo). Mice were housed at McMaster University's Central Animal Facility in standard cages in 12-h light/dark cycles with ad libitum access to water and their respective diets. C57/B16 mice from Jackson Laboratories were used as a wild type (WT) control. All experiments were approved by the McMaster University Animals Ethics Committee and conducted under appropriate Canadian guidelines for animal research.

Experimental groups All mice were fed standard rodent chow (chow diet; Harlan Teklad 8640 22/5), as a base diet with the exception of the group receiving a conventional substrate reduction therapy diet (% kcal of SRT diet being 93.2% fat, 6.4% protein and 0.4% carbohydrates; Envigo, TD.07797). The experimental groups are as follows: GAA knockout mice treated with enzyme replacement therapy (referred to as ERT group), GAA knockout mice treated with enzyme replacement therapy and administered a conventional substrate reduction therapy diet (referred to as ERT+ SRT group), GAA knockout mice treated with enzyme replacement therapy and administered a ketogenic agent comprising 1,3 butanediol (referred to as ERT+1,3 BD group) and GAA knockout mice treated with enzyme replacement therapy and administered an enhanced ketogenic composition comprising 1,3 butanediol and metabolic enhancing agents in the following amounts: 1% beetroot extract, 0.25% coenzyme Q10, 0.1% alpha lipoic acid and 1% creatine by weight, an additional 1000 IU/kg of vitamin E, 0.3% beta-hydroxy beta-methylbutyrate and 1% L-citrulline (referred to as ERT+1,3 BD+ME group). GAA mice receiving no treatment (referred to as GAA CON group) were used as controls as a comparison to the untreated disease progression and wild-type mice receiving no treatments (referred to as WT CON group) were used as controls as a comparison to a healthy state absent of known disease. Enzyme replacement therapy was comprised of bi-weekly intravenous injections of 40 mg/kg recombinant GAA enzyme (Myozyme; Genzyme). 30 minutes prior to every dose of Myozyme, mice were administered 5 mg/kg of the antihistamine diphenhydramine (Benadryl, Johnson and Johnson Inc.) intravenously. Treatment with 1,3 butanediol (Sigma Aldrich, B84785) was administered orally once daily via gavage at a dose of 7 mg/kg. The metabolic enhancing agents were formulated into the standard chow diet by Harlan Teklad.

Grip strength, motor coordination, and balance were evaluated prior to the introduction of the experimental diets. Motor coordination and balance were evaluated using a rotarod apparatus (Harvard Apparatus, MA), while forelimb grip strength was evaluated using a metal gripping bar attached to a DFIS-10 Chatillon digital force gage. Upon completion of the baseline testing, all groups were administered their respective experimental diets for a period of 8 weeks, when grip strength, motor coordination, and balance were re-evaluated as endpoint measures. Six days after the last GAA enzyme treatment, all mice were anaesthetised with isoflurane, sacrificed by exsanguination and tissues were harvested. Tissues for western blotting were immediately snap frozen in liquid nitrogen. The proteins p62, ubiquitin and mitochondrial complexes 1-5 were evaluated in quadriceps muscle using the following antibodies in 5% milk: p62 (Cell Signalling, Cat. #51145), ubiquitin (Enzo Life Sciences, Cat. #UG95100100) and Total OXPHOS Rodent WB Antibody Cocktail (Abcam, Cat. #ab110413). Autophagic buildup was determined using electron micrographs generated by the McMaster Electron Microscopy Facility. Autophagic buildup was evaluated using a scoring system, wherein two independent, blinded reviewers scored representative images using a scale system of 0=no buildup, 1=mild buildup, 2=moderate buildup, and 3=severe buildup for a total of 7 micrographs per group which were added into a per mouse total score out of 21.

To measure COX IV enzymatic activity, quadriceps muscle was homogenized in Lysing Matrix D tubes (MP Biomedicals, Solon, OH, USA) using the FastPrep-24 Tissue and Cell Homogenizer (MP Biomedicals, Solon, OH, USA) for 5×5-second cycles at a speed of 4.0 m/s with samples placed on ice for 5 minutes between cycles. Samples were homogenized in 20 volumes of buffer containing 70 mM sucrose, 220 mM mannitol, 10 mM HEPES, 1 mM EGTA, supplemented with protease inhibitors (Complete Mini®, Roche Applied Science, Laval, PQ, Canada). For COX IV activity, oxidized cytochrome c (Sigma C7752) was reduced by sodium dithionite in 0.05 M potassium phosphate buffer (KH2PO4, pH 7.4). Twenty microliters of muscle homogenate were added to 955 µL of 0.05 M potassium phosphate buffer and 30 µL of reduced cytochrome c in a cuvette that had been warmed to 37° C. The rate of oxidation of reduced cytochrome c was measured at 550 nm for 3 min at 37° C.

Results

Figure 1:
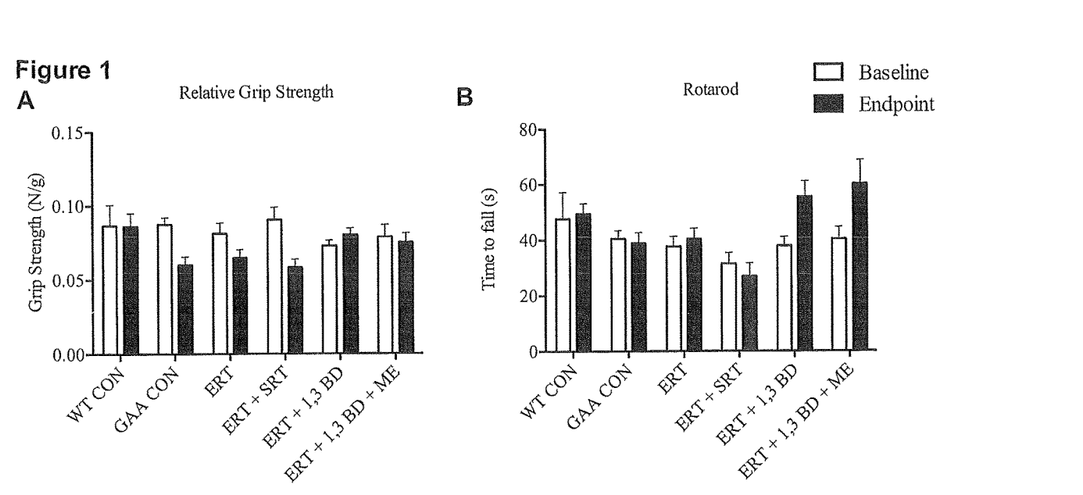
FIG. 1 graphically illustrates A) grip strength and B) rotarod performance in mice fed experimental diets for 8 weeks. WT CON, wild-type control; GAA CON, GAA control; ERT, GAA mice receiving ERT; ERT+SRT, GAA mice receiving ERT on a substrate reduction therapy diet; ERT+1,3 BD, GAA mice receiving ERT and 1,3 butanediol and; ERT+1,3 BD+ME, GAA mice receiving ERT, 1,3 butanediol and metabolic enhancing agents.

One of the primary symptoms associated with lysosomal storage disorders is a progressive worsening of muscle health. As can be observed in FIG. 1A, the forelimb grip strength of mice lacking the GAA enzyme (GAA CON) was reduced by 31% over the 8 week period, compared with no changes observed in the healthy WT (WT CON) mice as expected. Currently, the mainstay of treatment for Pompe disease is enzyme replacement therapy (ERT), wherein the GAA protein is administered intravenously to individuals having Pompe disease. Another common treatment for Pompe disease is substrate reduction therapy (SRT), where in one form of which an individual is administered a diet that is low in carbohydrates, with the goal of lowering glycogen buildup in the lysosomes by decreasing one of the biological precursors of glycogen. GAA mice in the ERT group experienced a 20% decline in grip strength, while mice the ERT+SRT group experienced a 35% decline in grip strength. Surprisingly, is was observed that muscle strength was relatively unchanged in GAA mice which were administered ERT in conjunction with either the ketogenic agent 1,3 butanediol (ERT+1,3 BD) or 1,3 BD and the metabolic enhancer (ME) (ERT+1,3 BD+ME). To further evaluate muscle function, we used a rotarod apparatus, which is known to measure muscle strength, motor coordination, and balance (FIG. 1B). We observed little or no change in the rotarod performance of mice in any of the WT CON, GAA CON, ERT or ERT+SRT groups. Similar to the findings of protection from grip strength loss, mice in the ERT+1,3 BD and ERT+1,3 BD+ME groups improved the duration of time in which they were able to balance on the rotarod apparatus by 46% and 49% respectively.

Figure 2:
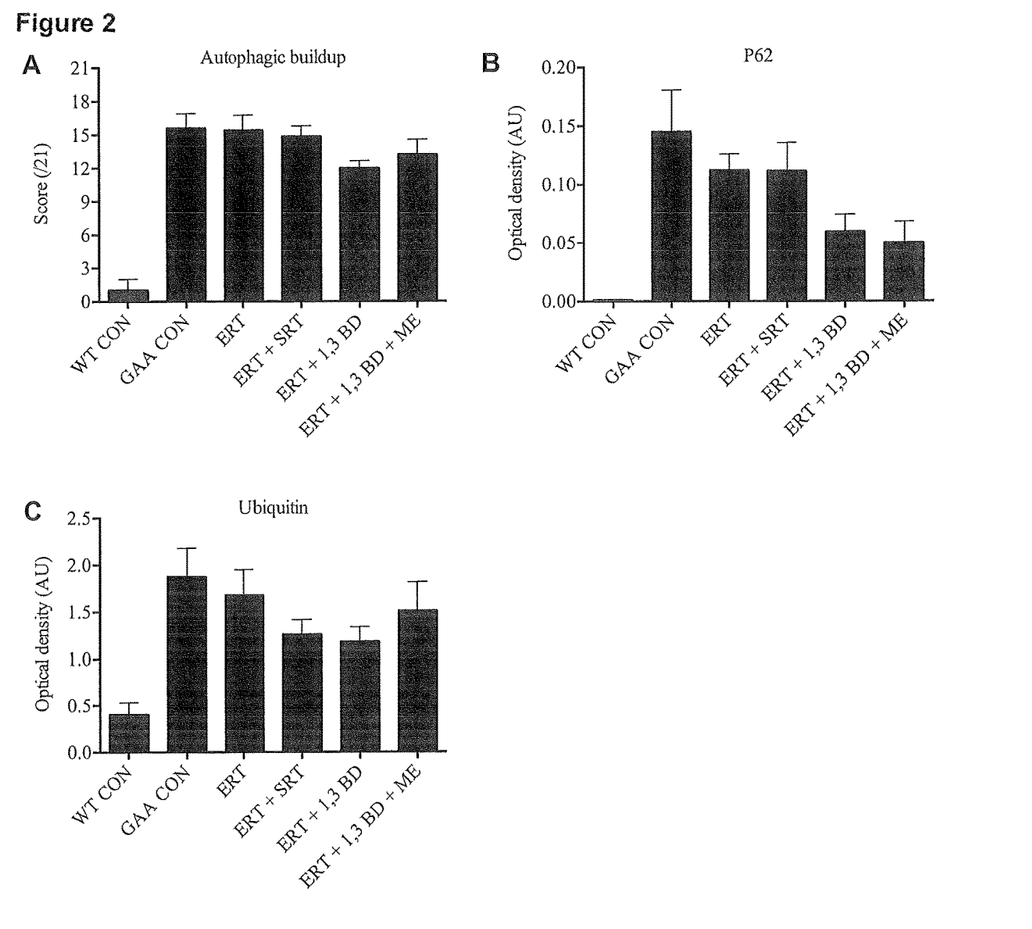
FIG. 2 graphically illustrates A) autophagic buildup, B) p62 protein and C) ubiquitin protein in mice fed experimental diets for 8 weeks. WT CON, wild-type control; GAA CON, GAA control; ERT, GAA mice receiving ERT; ERT+SRT, GAA mice receiving ERT on a substrate reduction therapy diet; ERT+1,3 BD, GAA mice receiving ERT and 1,3 butanediol and; ERT+1,3 BD+ME, GAA mice receiving ERT, 1,3 butanediol and metabolic enhancing agents.

One of the primary pathological events believed to lead to the progressive loss of muscle health in individuals with lysosomal storage disorders is the failure to carry out a sufficient amount of autophagic activity in the affected tissues. To determine if autophagic activity is improved in GAA mice treated with the ketogenic agent or the enhanced ketogenic composition, the level of autophagic buildup was evaluated in electron micrographs of skeletal muscle from each group (FIG. 2A). As would be expected, the amount of autophagic buildup was relatively negligible in the WT CON group (1/21). To the contrary, the amount of autophagic buildup in the GAA CON, ERT or ERT+SRT groups was scored at 16/21, 15/21 and 15/21, indicating a large buildup of intermediates in the autophagic pathway. Unexpectedly, the amount of autophagic buildup was lower in the ERT+1,3 BD (12/21) and ERT+1,3 BD+ME (13/21) groups, suggesting that autophagic activity was improved by these interventions. We next performed western blotting for p62 and ubiquitin, two proteins which are known to tag cellular materials for degradation. As expected, mice in the WT CON group had the lowest amount of p62 protein and mice in the GAA CON group had the highest expression (FIG. 2B). Both the ERT and ERT+SRT groups had p62 protein expression 23% lower than the GAA CON group. Promisingly, mice in the ERT+1,3 BD and ERT+1,3 BD+ME groups had the lowest p62 protein expression of the GAA mice, being 59% and 65% lower than GAA CON mice respectively. Protein expression levels of ubiquitin displayed a similar pattern to that of p62, but with the ERT+SRT group showing improvements comparable to those of the ERT+1,3 BD group (FIG. 2C).

Figure 3:
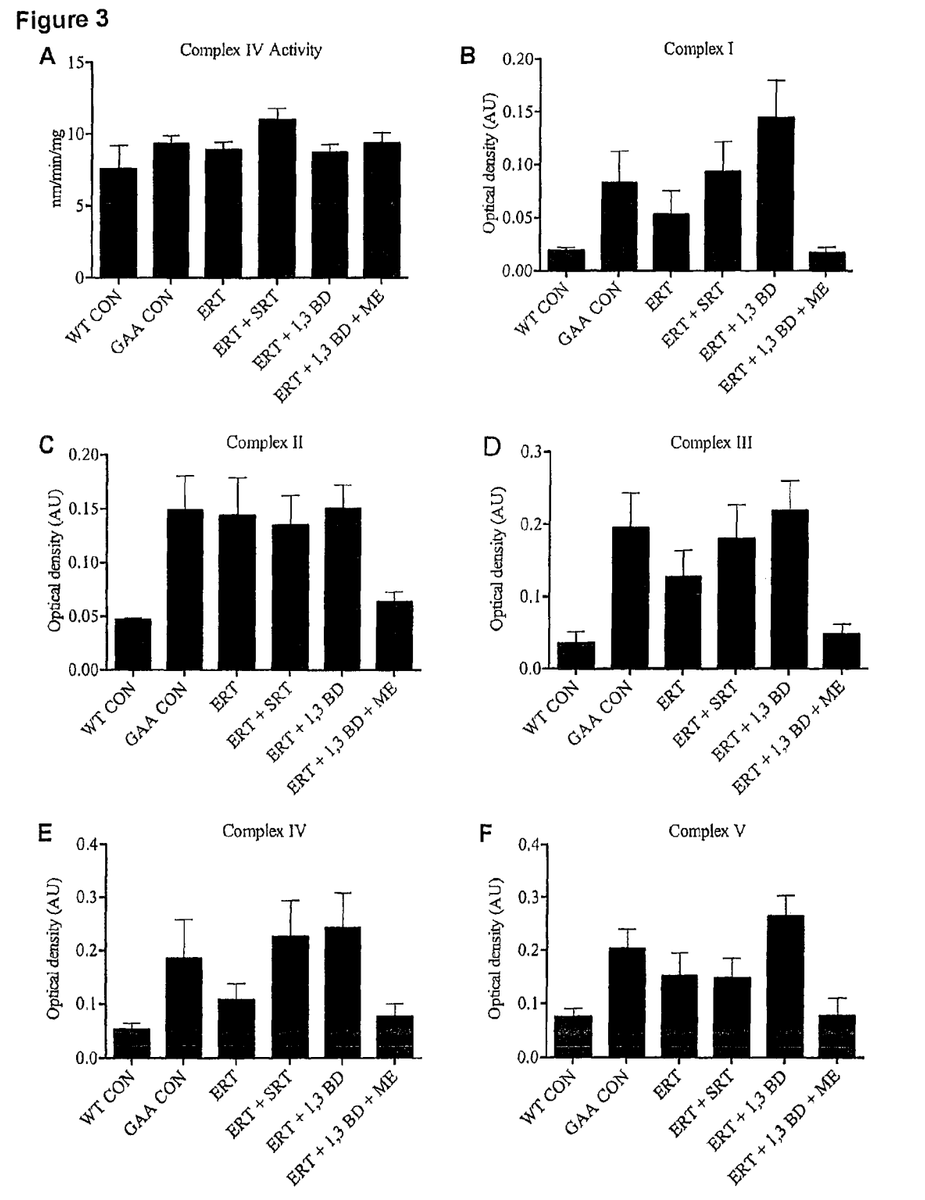
FIG. 3 graphically illustrates A) Complex IV enzyme activity, B) Complex I protein, C) Complex II protein, D) Complex III protein, E) Complex IV protein and F) Complex V protein in mice fed experimental diets for 8 weeks. WT CON, wild-type control; GAA CON, GAA control; ERT, GAA mice receiving ERT; ERT+SRT, GAA mice receiving ERT on a substrate reduction therapy diet; ERT+1,3 BD, GAA mice receiving ERT and 1,3 butanediol and; ERT+1,3 BD+ME, GAA mice receiving ERT, 1,3 butanediol and metabolic enhancing agents.

Another primary pathology that is associated with lysosomal storage disorders is the development of mitochondrial dysfunction. Since mitochondria act to maintain cellular energy levels for activities such as metabolism and locomotion, the mitochondrial dysfunction further exacerbates the other pathologies from the lysosomal storage disorder. To determine mitochondrial enzymatic activity, the activity of the Complex 4 protein was measured in skeletal muscle. In comparison to WT CON, mice in each of the groups having a GAA deficiency exhibited between a 15% and 45% higher amount of Complex 4 enzymatic activity (FIG. 3A). The protein abundance of the five mitochondrial enzyme complexes were next measured to determine how the enzymatic activity related to the mitochondrial protein content (FIGS. 3B-F). Generally, each of the groups lacking GAA activity had a substantial compensatory increase in each of mitochondrial complexes, with the levels being between 170-435% higher in GAA CON, between 103-250% higher in ERT, between 97-396% higher in ERT+SRT and between 219-647% higher in ERT+1,3 BD when compared to WT CON. Unexpectedly, the GAA mice in the ERT+1,3 BD+ME were largely protected against these GAA deficiency related increases in mitochondrial content, having protein levels for complexes 1-5 that were only between 0-48% higher than WT CON mice. Since the mitochondrial protein content of the mice in the ERT+1,3 BD+ME group was lower than all other GAA deficiency mice, while the enzymatic activity of all GAA mice were relatively the same, this further suggests that the ERT+1,3 BD+ME group also demonstrated a higher relative amount of mitochondrial enzymatic activity. Accordingly, when comparing the mean complex IV enzyme activity to the mean protein content of complex IV, the ratios were 65%, 43%, 66%, 41% lower for GAA CON, ERT, ERT+SRT and ERT+1,3 BD respectively, when compared to WT CON group. The ERT+1,3 BD+ME group was largely protected against this drop in enzyme activity to content ratio, experiencing a reduction of only 16% compared to WT CON, which suggests a preservation of relative mitochondrial capacity in this group. These findings demonstrate that the enhanced ketogenic composition may improve the mitochondrial capacity of mice having a lysosomal storage disorder by maintaining the mitochondria functioning in a state more similar to healthy control mice.

Collectively, the findings from this study surprisingly reveal that the administration of the ketogenic agent or the enhanced ketogenic composition to an individual having a lysosomal storage disorder, is an effective method for improving the muscle strength, autophagic activity and/or mitochondrial capacity of the individual in need thereof.

The present compositions and methods advantageously provide a means for treating a lysosomal storage disorder. In addition, the present compositions and methods have been scientifically validated to act synergistically with enzyme replacement therapy and may be used in an adjunctive manner with other primary treatment methods for treating a lysosomal storage disorder in an individual. The present compositions and methods may also be administered non-invasively and are inexpensive when compared to the cost of enzyme-based or chaperone-based therapies.

Relevant portions of references referred to herein are incorporated by reference.

The invention claimed is:

1. A product comprising a first dosage form consisting of a ketogenic agent and optionally one or more physiologically acceptable excipients, and a second dosage form consisting of one or more metabolic enhancing agents and optionally one or more physiologically acceptable excipients, wherein the ketogenic agent consists of 1,3-butanediol and the one or more metabolic enhancing agents consists of beet root extract, coenzyme Q10, creatine, alpha lipoic acid, vitamin E, beta-hydroxy-beta-methylbutyrate and citrulline, wherein the first and second dosage forms are formulated for administration separately in solid, semi-solid, liquid, semi-liquid, powder, suspension, emulsion, solution, ready-to-drink beverage, gel, bar, pill, tablet or capsule form and wherein the product treats a lysosomal storage disease.

2. The product of claim 1, wherein the metabolic enhancing agents additionally consist of green tea extract, green coffee bean extract and forskolin.

3. The product of claim 2, wherein the first dosage form comprises 1-80% by weight of ketogenic agent, and the second dosage form comprises 5-50% by weight of each of the green tea extract and the green coffee bean extract, 0.05-50% by weight forskolin, about 1-50% by weight of each of beet root extract, coenzyme Q10 and vitamin E, and 5-50% by weight of alpha lipoic acid, and 2-35% by weight of each of citrulline, creatine and beta-hydroxy-beta-methylbutyrate.

4. The product of claim 1, wherein the ketogenic agent is provided in the first dosage form in an amount sufficient to result in blood ketone body concentrations of 0.1 mM to about 25 mM, and the metabolic enhancing compounds provided in the second dosage form consist of 50-5000 mg of beetroot extract, 50-900 mg of coenzyme Q10, 50-900 mg alpha lipoic acid, 0.5-10 g creatine, 50-900 mg of vitamin E, 0.5-25 g of HMB and 0.5-25 g of citrulline.

5. The product of claim 4, wherein the metabolic enhancing compounds of the second dosage form additionally consist of 50-1000 mg of green tea extract, 50-1000 mg of green coffee bean extract, 15-100 mg of forskolin.

6. The product of claim 4, wherein the metabolic enhancing compounds provided in the second dosage form consist of 100-1000 mg of beetroot extract, 50-200 mg of coenzyme Q10, 50-500 mg alpha lipoic acid, 1-5 g creatine, 50-200 mg of vitamin E, 0.5-25 g of HMB and 0.5-25 g of citrulline.

7. A method of treating a lysosomal storage disease in a mammal, wherein the method comprises the step of administering to the mammal a product as defined in claim 1.

8. The method of claim 7, comprising administering to the mammal the ketogenic agent in a daily dosage of 0.01 g/kg body weight to 0.5 g/kg body weight.

9. The method of claim 7, wherein the ketogenic agent is administered in conjunction with lysosomal storage disease therapy.

10. The method of claim 7, comprising administering to the mammal a daily dosage of the ketogenic agent sufficient to result in a blood ketone body concentration of 0.1 mM to about 25 mM.

11. The method of claim 7, wherein the product is administered in conjunction with enzyme replacement therapy.

12. The method of claim 7, comprising administering to the mammal the ketogenic agent in a daily dosage of 0.01 g/kg body weight to 5 g/kg body weight.

13. The method of claim 7, which improves at least one of muscle function, autophagic activity and mitochondrial capacity in the mammal.

14. The method of claim 1, wherein the metabolic enhancing agents of the second dosage form consist of, 1-50% by weight of each of beet root extract, coenzyme Q10 and vitamin E, 5-50% by weight of alpha lipoic acid, and 2-35% by weight of each of citrulline and beta-hydroxy-beta-methylbutyrate.

15. The method of claim 7, wherein the lysosomal storage disease is Pompe disease.

\* \* \* \* \*